United States Patent
Hubbard et al.

(10) Patent No.: US 6,332,896 B1
(45) Date of Patent: *Dec. 25, 2001

(54) ORTHOPAEDIC IMPLANT WITH PROXIMAL COLLAR

(75) Inventors: Barry Hubbard, Draper, UT (US); Timothy McTighe, Chagrin Falls, OH (US); Jerry Kee, Palm Beach Gardens, FL (US); Paul Mraz, Cleveland, OH (US)

(73) Assignee: Ortho Development Corporation, Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/190,423

(22) Filed: Nov. 12, 1998

Related U.S. Application Data

(63) Continuation-in-part of application No. 09/037,643, filed on Mar. 10, 1998, now abandoned, which is a continuation of application No. 08/600,118, filed on Feb. 12, 1996, now Pat. No. 5,725,594, which is a continuation of application No. 08/274,956, filed on Jul. 14, 1994, now abandoned.

(51) Int. Cl.⁷ .................................................. A61F 2/34

(52) U.S. Cl. ............................................................ 623/23.24

(58) Field of Search .............................. 623/23.42, 23.46, 623/23.21, 23.24

(56) References Cited

U.S. PATENT DOCUMENTS

| | | |
|---|---|---|
| Re. 28,895 | 7/1976 | Noiles . |
| 2,719,522 | 10/1955 | Hudack . |
| 3,605,123 | 9/1971 | Hahn . |

(List continued on next page.)

FOREIGN PATENT DOCUMENTS

| | | |
|---|---|---|
| 426 096 | 6/1967 | (CH) . |
| 28 39 661 | 9/1979 | (DE) . |
| 3 125 657 | 1/1983 | (DE) . |
| 549 | 7/1978 | (EP) . |
| 2 472 374 | 7/1981 | (FR) . |
| 2 651 674 | 3/1991 | (FR) . |
| 83/02555 | 8/1983 | (WO) . |
| WO85/03426 | 8/1985 | (WO) . |

OTHER PUBLICATIONS

"In Vitro Study of Initial Stability of a Conical Collared Femoral Component", Fischer, Carter and Maloney, The Journal of Arthroplasty vol. 7 Supplement 1992.

"Horizontal Platform–Supported Total Hip System HPS II Achieving Physiological Stress Distribution with a Versatile Porous–Coated or Smooth–Stemmed System", Designed by Charles O. Townley, M.D., Depuy 1986.

(List continued on next page.)

*Primary Examiner*—David J. Isabella
(74) *Attorney, Agent, or Firm*—Clayton, Howarth & Cannon, P.C.

(57) ABSTRACT

A cementless femoral hip stem component. The hip stem component includes an elongate stem, a proximal body, and a collar disposed on the proximal body and extending outward therefrom in a sideways direction to form a ledge. The proximal body defines at least a majority of a frusto-conical shape. The ledge formed by the collar includes a tapered undersurface, beneath which extends the proximal body. The tapered undersurface of the ledge and the proximal body extend in different directions and thereby cooperatively define a double-flared contact surface configured to enable subsidable engagement of said double-flared contact surface with the femur at two different rates of subsidence within the femur. An abrupt, male corner is formed by the stem and the proximal body and is sufficiently abrupt to provide enhanced bone ingrowth stimulation.

28 Claims, 3 Drawing Sheets

U.S. PATENT DOCUMENTS

| | | |
|---|---|---|
| 3,782,373 | 1/1974 | Smythe . |
| 3,783,372 | 1/1974 | Smythe . |
| 3,808,606 | 5/1974 | Tronzo . |
| 3,840,904 | 10/1974 | Tronzo . |
| 3,848,272 | 11/1974 | Noiles . |
| 3,894,297 | 7/1975 | Mittlemeier et al. . |
| 3,943,576 | 3/1976 | Silvash . |
| 4,031,571 | 6/1977 | Heimke et al. . |
| 4,068,324 | 1/1978 | Townley et al. . |
| 4,206,516 | 6/1980 | Pilliar . |
| 4,304,011 | 12/1981 | Whelan, III . |
| 4,352,212 | 10/1982 | Greene et al. . |
| 4,514,865 | 5/1985 | Harris . |
| 4,530,114 | 7/1985 | Tepic . |
| 4,549,319 | 10/1985 | Meyer . |
| 4,619,659 | 10/1986 | Witzel . |
| 4,670,015 | 6/1987 | Freeman . |
| 4,718,916 | 1/1988 | Morscher . |
| 4,888,023 | 12/1989 | Averill et al. . |
| 4,944,762 | 7/1990 | Link et al. . |
| 5,062,854 | 11/1991 | Noble et al. . |
| 5,258,034 * | 11/1993 | Furlong et al. ............ 623/23 |
| 5,286,260 * | 2/1994 | Bolesky et al. ............ 623/23 |
| 5,314,489 | 5/1994 | Hoffman et al. . |
| 5,658,349 * | 8/1997 | Brooks et al. ............ 623/23 |
| 5,725,594 * | 3/1998 | McTighe et al. ............ 623/23 |
| 5,725,595 * | 3/1998 | Gustilo ............ 623/23 |
| 5,954,771 * | 9/1999 | Richelsoph et al. ............ 623/23 |

OTHER PUBLICATIONS

"New Jersey LCS Hip System", Depuy 1991.

Cook et al., Journal of Biomedical Materials Research, 18, 497–512, (1984).

Yue et al., Journal of Biomedical Materials Research, 18, 1043–1058, (1984).

Zimmer "Implant Metals" product catalog Rev.2A, (Sep., 1974).

"The Freeman Total Hip Systems," Corin Medical Limited, Gloucestershire, England, 1985.

Freeman, M.A.R., "Why Resect the Neck?", The Journal of Bone and Joint Surgery, vol. 68–B, No. 3, May 1986, pp. 346–349.

Biomet, Inc., osteocap rs™ Hip System Surgical Technique Brochure (1997)—.

Kirshner, C–2 Osteocap™ Hip (for date, etc. see explanation in IDS).

* cited by examiner

ORTHOPAEDIC IMPLANT WITH PROXIMAL COLLAR

This application is a continuation-in-part of U.S. application No. 09/037,643, filed Mar. 10, 1998 now abandoned, which was a continuation of U.S. application No. 08/600,118, filed Feb. 12, 1996, now U.S. Pat. No. 5,725,594, which was a continuation of U.S. application No. 08/274,956, filed Jul. 14, 1994, now abandoned.

BACKGROUND OF THE INVENTION

1. The Field of the Invention

The present invention relates generally to the field of artificial joints. The invention relates more particularly, but not exclusively, to a femoral cementless hip stem prosthesis that provides enhanced bone ingrowth stimulation and subsidable engagement within the femur.

2. The Background Art

It is known in the art to replace the hip joint with an artificial hip stem replacement. Numerous artificial implants are available that can be installed to replace the natural hip joint with an artificial ball and socket combination. A passage called the medullary canal is reamed or bored in the upper end of the femur. A stem or femoral component of an artificial implant is inserted into the reamed portion of the medullary canal in a secure, seated position. A neck member extends outward and away from the stem and terminates in a spherical knob for insertion into the acetabulum of the hip in rotational contact therewith about the three major orthogonal axes.

A hip prosthesis generally includes a collar or support plate disposed upon a proximal portion of the stem. The under surface of the support plate in most hip prostheses is flat and is disposed at an angle to the major direction of load, as shown for example in U.S. Pat. Nos. 5,314,489 (issued on May 24, 1994 to Hoffman et al.) and 4,888,023 (issued on Dec. 19, 1989 to Averill et al.). The planer geometry and angular orientation of prior art collars offer only limited capacity for force transfer. Prevailing hip stem philosophy dictates that the proximal portion of the stem provide the bulk of the force transfer, with the collar providing only minimal bone contact simply to prevent the stem from sinking too deeply into the femur. The thinking is that if the collar becomes fully seated it could prevent the proximal stem portion from fully engaging, resulting in less stress being transferred to the prosthesis/bone interface. Thus, prior art collars are designed to be flat and are configured so as to avoid fully-seated contact with the cortical bone.

The prior art femoral components are characterized by a number of disadvantages. The major load is transferred radially outward from the proximal stem portion in tension, generating "hoop stress" as it is referred to in the art. However, the femur is designed to accept loads from the hip joint in compression and not tension, and the tensile hoop stresses cause thigh pain in the patient. Further, the primary radial contact is less stable and allows for micromotion of the stem, making it difficult for the stem to achieve a position of stability. The micromotion decreases vital bone growth at the contact interface, further inhibiting stabilization. The planer geometry of the collar fails to permit settling of the collar in tandem with settling of the proximal stem portion which further inhibits stabilization. The flat collar actually tends to block settling. The prior art also fails to adequately inhibit osteolysis caused by wear debris introduced into the femoral canal at the site of the collar.

Relatively recent attempts to improve the state of the art include U.S. Pat. No. 4,944,762 (issued on Jul. 31, 1990 to Link et al., referred to herein as the "'762 patent"), which represents an attempt to improve the transfer of forces between the under surface of collar and the resection surface of the femur. However, such attempts are actually designed to prevent settling, as tacitly admitted in the '762 patent in col. 2 at lines 1–5. The '762 patent explains therein that the resection surface should be meticulously shaped to enable secure interlocking with the under surface. However, a secure interlock between the under surface of the collar and the resection surface prevents the prosthesis from settling to a position of stability. The '762 patent thus solves one problem but introduces others.

OBJECTS AND SUMMARY OF THE INVENTION

It is therefore an object of the present invention to provide a proximal prosthetic component for use in the replacement of joints.

It is another object of the invention, in accordance with one aspect thereof, to provide such a prosthetic component that replaces hoop stress with increased compressive force.

It is a further object of the invention to provide such a prosthetic component that is simple in design and manufacture.

It is an additional object of the invention, in accordance with one aspect thereof, to provide such a prosthetic component that enables increased surface area of contact with bone and corresponding reduction in the occurrence of gaps at the bone/prosthesis interface.

It is still another object of the invention, in accordance with one aspect thereof, to provide such a prosthetic component that reduces micromotion and thereby increases bone growth stimulation.

It is yet another object of the invention, in accordance with one aspect thereof, to provide such a prosthetic component which inhibits introduction of wear debris into the femoral canal.

It is a still further object of the invention, in accordance with one aspect thereof, to provide such a prosthetic component that provides enhanced bone ingrowth stimulation.

It is an additional object of the invention, in accordance with one aspect thereof, to provide such a prosthetic component that enables subsidable engagement within the femur.

The above objects and others not specifically recited are realized in a specific illustrative embodiment of a cementless femoral hip stem component. The hip stem component includes an elongate stem, a proximal body, and a collar disposed on the proximal body and extending outward therefrom in a sideways direction to form a ledge. The proximal body defines at least a majority of a frustoconical shape. The ledge formed by the collar includes a tapered undersurface, beneath which extends the proximal body. The tapered undersurface of the ledge and the proximal body extend in different directions and thereby cooperatively define a double-flared contact surface configured to enable subsidable engagement of said double-flared contact surface with the femur at two different rates of subsidence within the femur. An abrupt, male corner is formed by the stem and the proximal body and is sufficiently abrupt to provide enhanced bone ingrowth stimulation.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION

Figure 1:
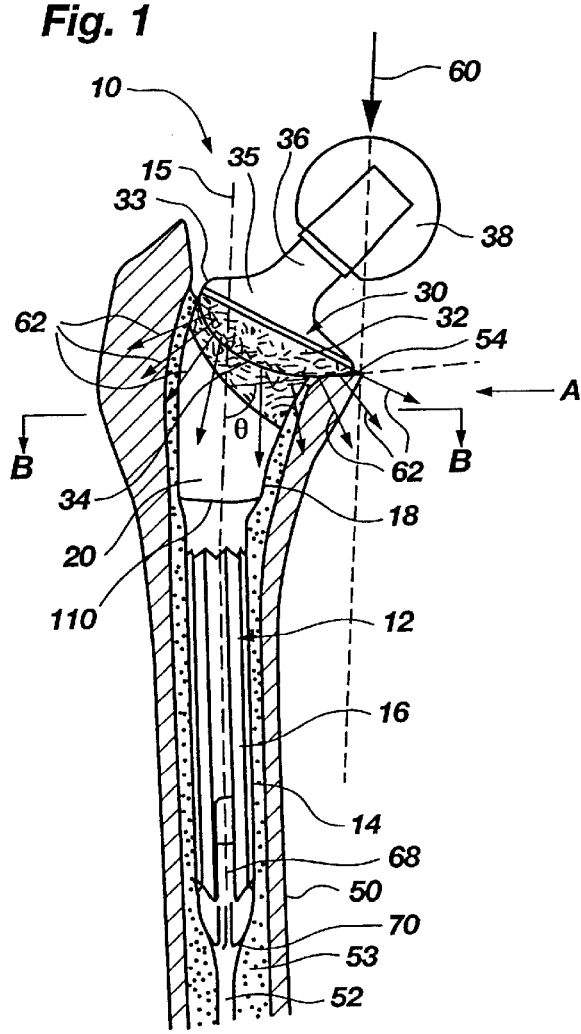
FIG. 1 illustrates a side view of a hip prosthesis made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Referring now to FIG. 1, there is shown a prosthesis generally designated at 10. The prosthesis 10 includes an elongate stem 12 and a collar or support plate 30 attached thereto. The stem 12 includes a fluted distal section 14 and an opposing proximal section 18, centered generally around a long axis 15 of the stem. The fluted distal section 14 preferably includes a slot 68 extending along the long axis 15. The distal section 14 has a plurality of longitudinal flutes 16 formed therein, and the proximal section 18 includes a proximal exterior surface 20 defining a conical contact surface. The term "distal" as used herein refers to the portion of the prosthesis 10 positioned farthest within a femoral canal 52 of a femur 50. The stem 12 preferably terminates in a substantially pointed end 70 in the distal direction.

The collar, designated generally at 30, includes a tapered under surface 32. The taper on under surface 32 preferably forms a circumferential frustoconical surface in either symmetrical or asymmetrical fashion, but may be configured as any non-planar, generally tapering surface. The proximal surface 20 of the stem meets at a proximal edge thereof with the under surface 32 of the collar to form a circumferential transition section 34. The transition section 34 is preferably rounded so as to be characterized by an absence of corners and points, but may be alternatively defined by a corner. The proximal surface 20 of the stem and the under surface 32 of the collar both flare outwardly in a distal to proximal direction. These surfaces 20 and 32 may alternatively define any curvilinear or other nonplaner shape representing an average surface contour which flares outwardly in a distal to proximal direction. The collar 30 further includes a top side 35 configured to support a neck 36 having a hip ball 38 or other joint motion surface attached thereto.

Figure 1A:
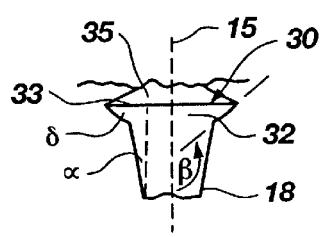
FIG. 1A illustrates a fragmented front view of the hip prosthesis of FIG. 1.

It is preferred that the under surface 32 be flared at a greater degree of flare than the proximal surface 20 so as to form an angle therewith of less than 180 degrees. Referring now to FIG. 1A, there is shown a fragmented front view of part of the proximal section 18 and the collar 30 of FIG. 1 from the perspective of the direction shown by arrow A. The under surface 32 forms an angle $\delta$ with respect to a plane 33 inclined at an angle with respect to the long axis 15. The angle $\delta$ is preferably within a range of approximately twenty five to thirty five degrees, and most preferably thirty degrees. The top surface 35 may itself form the plane 33. The proximal surface 20 is flared at an angle $\alpha$, which is preferably about five degrees. Accordingly, the angle $\alpha$ shown in FIG. 1A causes the proximal section 18 to constitute a somewhat conical stem surface, and the angle $\alpha$ causes the undersurface 32 to constitute a somewhat conical plate surface, as shown in FIG. 1A.

Figure 1B:
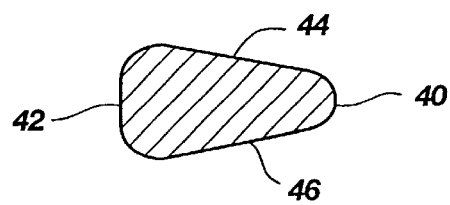
FIG. 1B illustrates a cross sectional view of a proximal portion of the hip prosthesis of FIG. 1, taken along section B—B

Referring now to FIG. 1B, there is shown a cross sectional view of the proximal section 18, taken along section B—B. The proximal section 18 includes a medial side 40, lateral side 42, anterior side 46 and posterior side 44, corresponding to the medial, lateral, anterior and posterior directions as known in the medical art. Although it is preferred that the entire proximal surface 20 be flared, flaring may alternatively be confined to certain parts thereof such as to the anterior and posterior sides 46 and 44. In addition, flaring of the under surface 32 of the collar 30 may be alternatively confined to certain parts thereof, such as to the medial, anterior and posterior sides.

Figure 2:
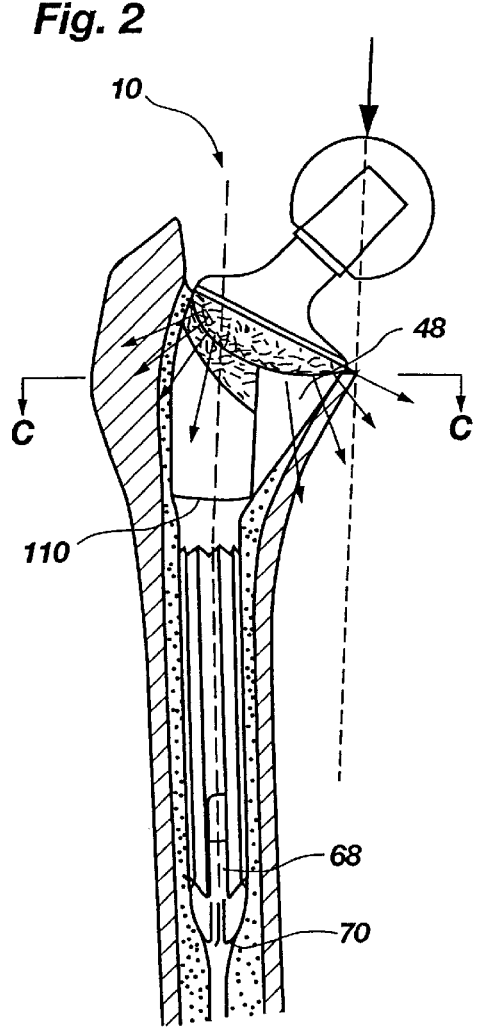
FIG. 2 illustrates a side view of an alternative embodiment of the hip prosthesis of FIG. 1.
Figure 2A:
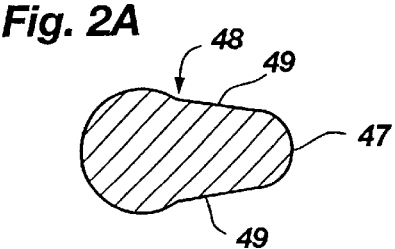
FIG. 2A illustrates a cross sectional view of a proximal portion of the hip prosthesis of FIG. 2, taken along section C—C.

An alternative embodiment of the prosthesis 10 is shown in FIG. 2. Representative reference numerals provided in FIG. 1 should be read to apply also to FIG. 2. A medial triangular projection 48 is disposed to form the medial portion of the proximal section 18. The medial triangular projection 48 includes a rounded medial end 47 as shown in FIG. 2A. The rounded medial end 49 intercouples opposing sides 49 which flare outwardly from the medial end in medial to lateral directions. It can thus be seen by inspection of FIG. 2A that a cross section of the medial triangular projection 48 taken along horizontal plane section C—C, which is perpendicular to the long axis 15 of the stem 12, defines a conical section having a rounded tip.

The prosthesis is particularly adapted for use as a hip stem prosthesis. In use, the distal section 14 of the stem 12 is inserted in the medullary canal 52 of the femur 50. The femur 50 has been reamed and otherwise prepared beforehand in a manner known to those skilled in the art. The stem 12 is pressed into the canal 52 until the under surface 32 comes to rest upon hard, load-bearing cortical bone 54 of a lesser trochanter of the femur 50. The hip ball 38 is placed upon the neck 36 and inserted into the acetabulum (not shown) of the hip so as to function as a joint motion surface. The proximal conical surface 20 subsidably engages against side walls of the hollow interior medullary canal 52. Similarly, the conical under surface 32 subsidably engages against the load-bearing cortical bone 54.

It is to be understood that the under surface 32 is specifically designed to contact a substantial amount of the hard cortical bone 54 but still allow for subsidence or settling of the prosthesis 10. A non-limiting example of this subsidability is to form portions of the under surface 32 such that they are maintained at an angle relative to the long axis 15 which is greater than ninety degrees. For example, a medial portion of the under surface 32 preferably resides at an angle Θ relative to the long axis 15 which is greater than ninety degrees, as shown most clearly in FIG. 1. Anterior and posterior portions of the under surface 32 reside at an angle β relative to the long axis 15, the angle β also being preferably greater than ninety degrees.

The angled relationships achieved by the flared geometry of the under surface 32 enable it to simultaneously accomplish two important functions: (i) transfer an increased amount of load 60 to the cortical bone 54 in compression, and (ii) subsidably engage with the cortical bone 54 so as to settle to a position of stability. The flared geometry of the proximal conical surface 20 also enhances subsidable contact. The overall effect is that the proximal conical surface 20 and the conical under surface 32 collectively form a unitary double-flared contact surface for maximum surface area of contact. Since both the proximal surface 20 and the under surface 32 are conical or otherwise flared, they provide increased surface area of contact with the femur 50 and permit settling of the prosthesis 10 to a position of stability. When the angles Θ of FIG. 1 and/or β of FIG. 1A are closer to ninety degrees, more of the load 60 is transferred to the femur 50 in the form of compression. The idea is to increase the amount of contact between the under surface 32 and the cortical bone 54, but in a subsidable manner.

It will be appreciated that the increased surface area of contact provided by the prosthesis 10, the settling capacity of both the proximal surface 20 and the under surface 32, and the corresponding stability provide a number of advantages over the prior art. Since the collar 32 is intended to contact the cortical bone 54 instead of avoid contact, the collar functions as a cap to substantially close off the upper portion of the femur 50. This capping action inhibits the introduction of osteolysis-causing wear debris into the medullary canal 52.

The increased proximal surface engagement of the cooperating conical surface 20 and under surface 32 is much more stable than the primarily tensile load transfer of prior art hip stems. Those skilled in the art will appreciate that the increased stability stimulates the bone for increased bone growth in accordance with Wolff's law, which provides that new bone growth is stimulated in direct proportion to the degree of loading upon the bone. The increased bone growth further enhances the stability of the prosthesis 10. Applicants have found that the increased stability operates to decrease micromotion of the prosthesis up to a factor of 10. In other words, where some prior art stems exhibit micromotion in certain areas of about 1000 microns, applicants' hip stem would respond with 100 microns of micromotion or less. When micromotion is substantially greater than 100 microns, the fibrous soft tissue interface between the inner medullary bone 53 and the prosthesis 10 is prevented from adhering to the prosthesis in new growth. This decreases stability and weakens the femur 50, and the present invention avoids such disadvantages because it loads the bone as much as possible in a stable manner for the other reasons discussed above.

The advantages discussed above can be present even if the circumferential transition section 34 defines a sharp corner. Desirable settling action of the prosthesis 10 can be enhanced by rounding the transition section 34 with a radius of curvature such that it is characterized by an absence of corners and points.

The prosthesis 10 is thus advantageously adapted for use as a cementless prosthesis. There is no question that bone cement has made and continues to make a significant contribution to the success of total hip replacements. However, it is important to recognize its inherent biological and mechanical limitations (low modulus, low fatigue strength, and toxicity). The present invention operates to transfer the load 60 into the femur 50 as compression, in accordance with the natural design of the hip joint and femur.

The present invention is also more user friendly. Too often the general orthopedist does not appreciate the required implantation technique for a given prosthesis design. Some tend to overextend indications. The lack of a full understanding of prosthesis design features and required surgical implantation techniques has led some surgeons to implant hip stem prosthesis incorrectly, in some cases predisposing the prosthesis to failure. It has been established that an important part of prior art hip stem prostheses is based on the concept of shaping the resection surface of the femur to correspond precisely to the under surface of the collar, so that the under surface interlocks securely with the resection surface (see U.S. Pat. No. 4,944,762 at col. 2, lines 1–5). This of course not only prevents the prosthesis from settling to a position of stability, it also requires precision cutting by the surgeon with little tolerance. However, since the present invention does not require interlocking but is specifically designed to enhance settling action, a less than perfect resection surface of the femur will not predispose the device to failure.

Figure 3:
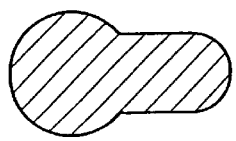
FIG. 3 illustrates a cross sectional view of prior art hip stem geometry.

The medial triangular portion 48 of FIG. 2, although optional, offers a number of additional advantages, including additional surface area of contact. The increased surface contact provides increased rotational stability of the prosthesis 10. The medial to lateral flaring sides 49, shown in FIG. 2A, have been found by applicants to offer improved stability over the prior art "keyhole" geometry shown in FIG. 3.

Figure 4:
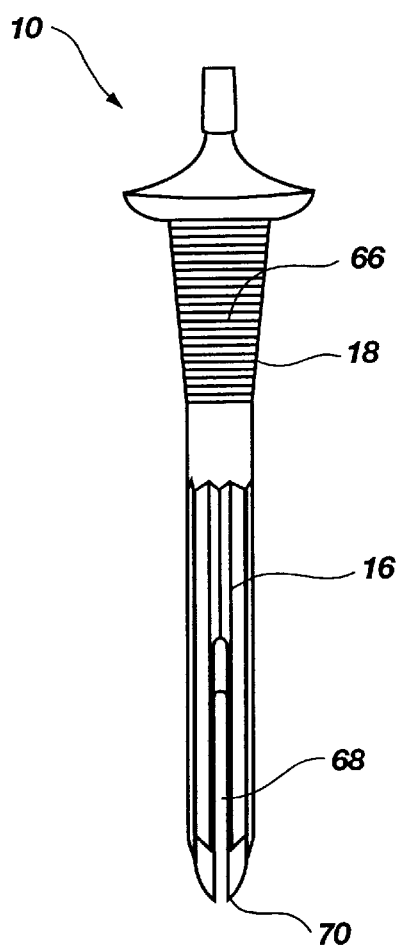
FIG. 4 illustrates a front view of an alterative embodiment of the hip prosthesis of FIG. 1.
Figure 5:
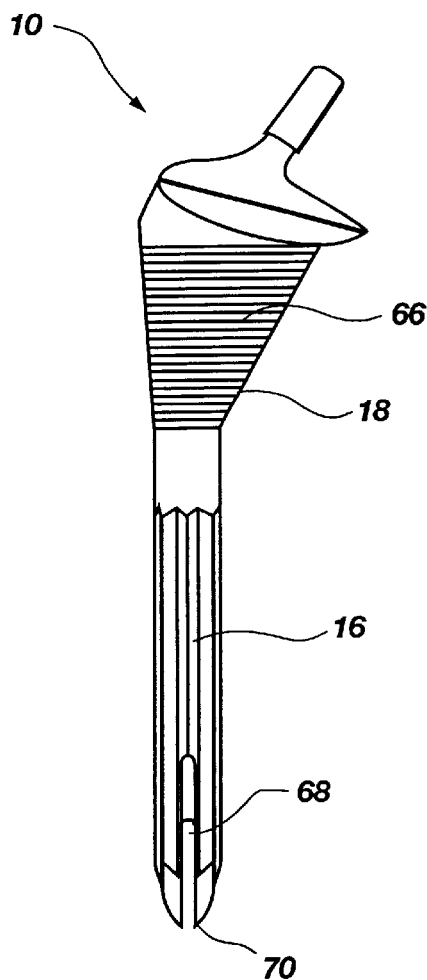
FIG. 5 illustrates a side view of the hip prosthesis of FIG. 4.

Referring now to FIGS. 4–5, it is to be understood that any embodiment of the prosthesis 10 may include circumferential terraces 66 formed in the proximal section 18. It will be appreciated that the terraces 66 are forced into engagement with the surrounding intra medullary bone 53 to block rotational movement of the prosthesis 10, and to stimulate supporting bone growth therearound. The longitudinal flutes 16 also operate to provide rotary stability to the prosthesis 10 relative to the femur 50.

The prosthesis 10 may be formed as a unibody device, or a modular device in the alternative. For example, the proximal section 18 could be a separable component from the rest of the stem 12, and the collar 30 could be a separable component from the proximal section 18. This alternative offers the advantage of selectively sizing two or more components to more precisely tailor the fit of the resulting total prosthesis to the specific internal contours of the patient.

A preferred method for replacing a joint in a patient in accordance with the principles of the present invention includes the steps of:

(a) selecting a prosthetic component including a flared proximal section and a flared plate section extending circumferentially outward from said flared proximal section such that said flared proximal and plate sections cooperatively form a unitary double-flared contact surface, and a joint motion surface extending outward from the plate section;

(b) inserting the prosthetic component into a medullary cavity of a first bone such that the flared proximal section subsidably engages with side walls of the medullary cavity in tandem with the flared plate section subsidably engaging with a load-bearing portion of the first bone such that the double-flared contact surface enables settling of the prosthetic component against contacting portions of the medullary cavity and load-bearing portion to a position of stability;

(c) inserting the joint motion surface into a second bone member to thereby enable load transfer between the first bone and the second bone member;

(d) preparing the load-bearing surface of the first bone and placing the flared plate section into contact therewith such that contacting portions of said flared plate section with the load-bearing surface form an angle with a long axis of the medullary cavity which is greater than ninety degrees to thereby enhance settling action of said flared plate section against said load-bearing surface.

The "flared plate section" referred to above as part of the preferred method refers to the under surface 32 shown in FIG. 1, which has been described herein as having "a greater degree of flare than the proximal surface 20." Thus, the medial section of the flared plate or under surface 32 extends outwardly from the proximal portion 18 of the stem 12 to define a type of overhang ledge relative to said proximal portion 18 as shown in FIG. 1. As also shown in FIG. 1, said overhang is greater than any overhang which might extend outwardly from a lateral portion of said proximal portion 18, the medial, lateral, anterior and posterior locations being described above in conjunction with FIG. 1B. As further shown in FIG. 1, there is preferably no overhang on the lateral side of the prosthesis 10.

It is to be understood that the phrase "greater than any overhang which might extend outwardly from a lateral portion of said proximal portion" as used herein shall refer broadly to lateral portions with overhangs as well as lateral portions without overhangs. The key is that the overhang defined by the flared plate or under surface 32 on the medial side is greater than any overhang extending outwardly from the lateral side, if any, this concept being supported by the overhang produced by the under surface 32 in FIG. 1. It is also shown in FIG. 1 that the under surface 32 forms an angle Θ relative to the long axis 15 than resides somewhere within a range between ninety degrees and one hundred twenty degrees, and preferably less than one hundred degrees.

Figure 6:
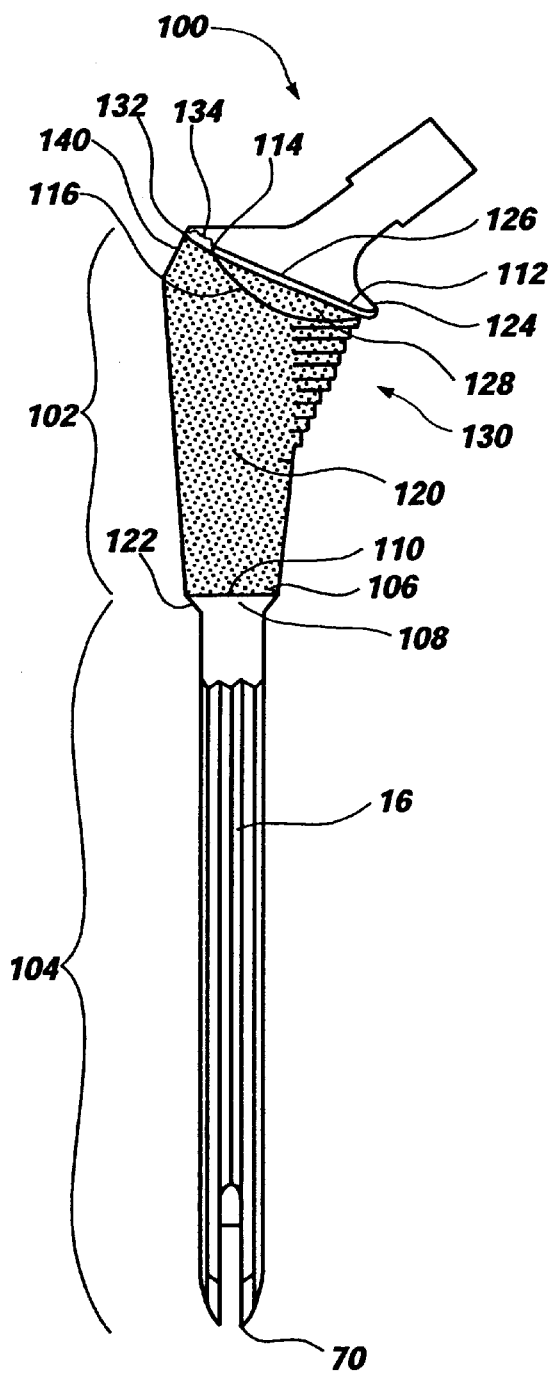
FIG. 6 illustrates a side view of another alternative embodiment of the hip stem prosthesis of FIG. 1.

Referring now to FIG. 6, there is shown another embodiment of the invention in the form of a hip prosthesis designated generally at 100. The prosthesis 100 includes a proximal body 102, and a stem 104 disposed on a lower portion of the proximal body 102 and extending therefrom in a distal direction. The proximal body 102 is coated with tiny, spherical beads 120 that are fused about the exterior surface of the proximal body 102.

The stem 104 defines a longitudinal axis, and a distal-most portion 106 of the proximal body 102 is substantially wider than a proximal-most portion 108 of the stem 104 such that the stem and the proximal body cooperatively form a male corner 110 therebetween. The male corner 110 defines a boundary between said distal-most portion 106 of the proximal body 102 and said proximal-most portion 108 of the stem 104.

The male corner 110, being located where it is as a boundary between the proximal body 102 and the stem 104, is thus positioned to induce bone ingrowth because of its prominent, protruding nature in a key axial area of the prosthesis 100. The structural aspect of the male corner 110 is such that it comprises an abrupt transition between the stem 104 and the proximal body 102 that is sufficiently abrupt in dimension and configuration to stimulate the bone ingrowth, to a greater degree than bone ingrowth occurring about the stem 104, when implanted within a hollow interior portion of a bone such as a femur.

This is possible because the distal-most portion 106 of the proximal body 102 is substantially wider in all dimensions than the stem, i.e. in both the medial-lateral directional dimension and in the anterior-posterior directional dimension. The male corner 110 preferably comprises a circumferential male corner, and more preferably defines a circle. The male corner 110 protrudes radially outwardly from the stem 104 by a distance sufficient to stimulate and increase the bone ingrowth mentioned above. Preferably, the distal-most portion 106 of the proximal body 102 is at least two millimeters wider than the proximal-most portion 108 of the stem 104, and may be designed to be three millimeters or four millimeters or more wider than said stem 104.

A collar 112 is disposed on the proximal body 102. The collar 112, proximal body 102 and stem 104 cooperatively define a first collective length, and wherein the male corner 110 is spaced apart from a proximal-most portion 114 of the collar 112 by a distance of at least one-fifth of said first collective length, in order to stimulate bone ingrowth at a location along the length of the prosthesis 100 that will promote key stability and integration of the prosthesis 100 with a femur. The prosthesis 100 may be designed such that the male corner 110 is spaced apart from the proximal-most portion 114 of the collar 112 by a distance of at least one-fourth, or even one-third, of the first collective length so described above.

The collar 112 extends outward from the proximal body 102 in a sideways direction with respect to the longitudinal axis of the stem 104 to thereby define a ledge. The ledge so defined, and the proximal body 102, cooperatively form an abrupt female corner 116 therebetween.

The stem 104 preferably tapers inwardly from the male corner 110 in a proximal-to-distal direction to thereby define a concave area 122. The tapering of the stem 104 preferably further comprises a circumferential, radial inward tapering such that the concave area 122 is a circumferential concave area, for further enhanced bone ingrowth.

Figure 7:
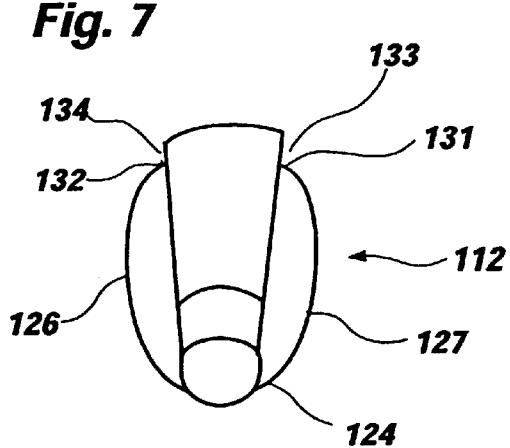
FIG. 7 illustrates a top view of the prosthesis of FIG. 6.

The collar 112 extends outward from the proximal body 102 in a medial direction and in a posterior direction and in an anterior direction such that the overhang ledge formed by the collar 112 comprises a tri-directional, continuous medial-posterior-anterior overhang, in which portion 124 comprises the medial overhang and portion 126 forms the anterior overhang. In FIG. 7 the posterior overhang 127 is shown.

The tri-directional overhang has a flared, non-planer undersurface 128, and the proximal body 102 preferably has a flared exterior surface defining a non-cylindrical, flared shape such that said proximal body 102 and the flared, non-planer undersurface 128 cooperatively define a double-flared contact surface to thereby enable subsidable engagement of said double-flared contact surface at two different rates of subsidence within the femur. The flared exterior surface of the proximal body 102 defines at least a majority of a frustoconical shape, in that essentially all exterior portions of the proximal body 102 except for the stepped portion 130 form a majority portion of a frustoconical shape.

The undersurface 128 preferably comprises a rounded, bowl-shaped, non-planer undersurface. The bowl-shaped nature of the undersurface 128 helps center the prosthesis 100 within the femur. The undersurface 128 is bowl-shaped in that it tapers upwardly along all, or substantially all, of its perimeter.

Referring to FIGS. 6 and 7, the collar 112 is preferably characterized by an absence of any lateral overhang, in that the posterior overhang 127 (not shown in FIG. 6) and the anterior overhang 126 each terminate in the lateral direction at a terminal posterior point 131 (not shown in FIG. 6) and a terminal anterior point 132, respectively, along posterior and anterior sides of the proximal body 102, respectively, to thereby define a spacial posterior gap 133 (not shown in FIG. 6) and a spacial anterior gap 134 between the lateral side of the proximal body 102 and said terminal posterior point and terminal anterior point 132, respectively. This absence of a lateral overhang, and the existence of the posterior gap and the anterior gap 134, help prevent interference to the proper centering and subsiding settlement of the prosthesis 100 into a position of stability.

A majority length of the stem 104 defines a common, non-varying radius. Also, as shown in FIG. 6, the prosthesis 100 includes an upper lateral slanted face 140 that is distinctly steeper than the opposing medial slanted face or stepped portion 130.

The present invention represents a significant advance in the field of artificial joint prostheses. It is to be understood that although the present invention has been illustrated herein in the context of hip joint replacement, it is equally applicable to any prosthetic application. For example, an embodiment of the present invention as described and claimed herein could be used to replace the knee joint. The disadvantages in the prior art noted above and others not discussed are overcome to a significant degree by the present invention. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A prosthetic component implantable into a hollow interior portion of a first bone, said prosthetic component comprising:
    a proximal body;
    a stem disposed on a lower portion of the proximal body and extending therefrom in a distal direction, said stem having a longitudinal axis, wherein a distal-most portion of the proximal body is wider than a proximal-most portion of the stem such that the stem and the proximal body cooperatively form a convex corner therebetween, said convex corner defining a boundary between said distal-most portion of the proximal body and said proximal-most portion of the stem; and
    a collar disposed on the proximal body and extending outward therefrom in a sideways direction with respect to the longitudinal axis of the stem to thereby define a ledges;
    wherein the collar extends outward from the proximal body in a medial direction and in a posterior direction and in an anterior direction such that the ledge comprises a tri-directional, continuous medial-posterior-anterior overhang;
    wherein the overhang includes a rounded, bowl-shaped, nonplaner undersurface.

2. The prosthetic component of claim 1, wherein the ledge and the proximal body form an abrupt concave corner therebetween.

3. The prosthetic component of claim 1, wherein the male corner comprises a surface irregularity dimensioned to provide bone ingrowth.

4. The prosthetic component of claim 1, wherein the distal-most portion of the proximal body is wider in a medial-lateral dimension than the stem in said medial-lateral dimension.

5. The prosthetic component of claim 1, wherein the convex corner comprises a circumferential convex corner.

6. The prosthetic component of claim 1, wherein the circumferential male corner defines a circle.

7. The prosthetic component of claim 1, wherein the convex corner protrudes a distance radially outwardly from the stem to stimulate bone ingrowth.

8. The prosthetic component of claim 1, wherein the distal-most portion of the proximal body is at least two millimeters wider than the proximal-most portion of the stem.

9. The prosthetic component of claim 1, wherein the distal-most portion of the proximal body is at least three millimeters wider than the proximal-most portion of the stem.

10. The prosthetic component of claim 1, wherein the distal-most portion of the proximal body is at least four millimeters wider than the proximal-most portion of the stem.

11. The prosthetic component of claim 1, wherein the collar, proximal body and stem cooperatively define a first collective length, and wherein the convex corner is spaced apart from a proximal-most portion of the collar by a distance of at least one-fourth of said first collective length.

12. The prosthetic component of claim 1, wherein the collar, proximal body and stem cooperatively define a first collective length, and wherein the convex corner is spaced apart from a proximal-most portion of the collar by a distance of at least one-fifth of said first collective length.

13. The prosthetic component of claim 1, wherein the collar, proximal body and stem cooperatively define a first collective length, and wherein the convex corner is spaced apart from a proximal-most portion of the collar by a distance of at least one-third of said first collective length.

14. The prosthetic component of claim 1, wherein the stem tapers inwardly from the convex corner in a proximal-to-distal direction to thereby define a concave area.

15. The prosthetic component of claim 14, wherein the tapering of the stem further comprises a circumferential, radial inward tapering to thereby define a circumferential concave area.

16. The prosthetic component of claim 1, wherein the collar extends outward from the proximal body in a medial direction and in a posterior direction and in an anterior direction such that the ledge comprises a tri-directional, continuous medial-posterior-anterior overhang.

17. The prosthetic component of claim 1, wherein the overhang has a flared, non-planer undersurface, and wherein the proximal body has a flared exterior surface defining a non-cylindrical, flared shape such that said proximal body and the flared, non-planer undersurface of the overhang cooperatively define a double-flared contact surface to thereby enable subsidable engagement of said double-flared contact surface at two different rates of subsidence.

18. The prosthetic component of claim 17, wherein the flared exterior surface of the proximal body defines at least a majority of a frustoconical shape.

19. The prosthetic component of claim 1, wherein the collar extends outward from the proximal body in a medial direction and in a posterior direction and in an anterior direction to thereby form a tri-directional, continuous medial-posterior-anterior overhang, said collar being characterized by an absence of any lateral overhang and wherein the posterior and anterior portions of said overhang each terminate in the lateral direction at a terminal posterior point and a terminal anterior point, respectively, along posterior and anterior sides of the proximal body, respectively, to thereby define a spacial posterior gap and a spacial anterior gap between the lateral side of the proximal body and said terminal posterior point and terminal anterior point, respectively.

20. The prosthetic component as defined in claim 1, wherein a majority length of the stem defines a non-varying radius.

21. A prosthetic component implantable into a hollow interior portion of a first bone, said prosthetic component comprising:
    a proximal body having a lateral side;
    a stem disposed on a lower portion of the proximal body and extending therefrom in a distal direction, said stem having a longitudinal axis, wherein an average width of the proximal body in a medial-lateral dimension is wider than the stem; and
    a collar disposed on an upper portion of the proximal body and extending outward therefrom in a medial direction and in a posterior direction and in an anterior direction to thereby form a tri-directional, continuous medial-posterior-anterior overhang, said collar being characterized by an absence of any lateral overhang and wherein the posterior and anterior portions of said overhang each terminate in the lateral direction at a terminal posterior point and a terminal anterior point, respectively, along posterior and anterior sides of the proximal body, respectively, to thereby define a spacial posterior gap and a spacial anterior gap between the lateral side of the proximal body and said terminal posterior point and terminal anterior point, respectively.

22. The prosthetic component of claim 21, wherein a distal-most portion of the proximal body is wider than a proximal-most portion of the stem such that the stem and the proximal body cooperatively form a convex corner therebetween, said male convex defining a boundary between said distal-most portion of the proximal body and said proximal-most portion of the stem.

23. The prosthetic component of claim 22, wherein the convex corner comprises a circumferential convex corner.

24. The prosthetic component of claim 22, wherein the circumferential convex corner defines a circle.

25. A prosthetic component implantable into a hollow interior portion of a first bone, said prosthetic component comprising:
    a proximal body having a lateral side and a plurality of circumferential terraces;
    a stem disposed on a lower portion of the proximal body and extending therefrom in a distal direction, said stem having a longitudinal axis and a slot extending along said longitudinal axis, wherein an average width of the proximal body in a medial-lateral dimension is wider than the stem, and said stem terminates in a substantially pointed end; and
    a collar disposed on an upper portion of the proximal body and extending outward therefrom in a medial direction and in a posterior direction and in an anterior direction to thereby form a tri-directional, continuous medial-posterior-anterior overhang, said collar being characterized by an absence of any lateral overhang;
    wherein a majority length of the stem defines a common, non-varying radius.

26. The prosthetic component of claim 24, wherein at least seventy percent of a continuous length of the stem defines a common, non-varying radius.

27. The prosthetic component of claim 24, wherein at least eighty percent of a continuous length of the stem defines a common, non-varying radius.

28. A prosthetic component implantable into a hollow interior portion of a first bone, said prosthetic component comprising:
    a proximal body;
    a stem disposed on a lower portion of the proximal body and extending therefrom in a distal direction, said stem having a longitudinal axis, wherein a distal-most portion of the proximal body is wider than a proximal-most portion of the stem such that the stem and the proximal body cooperatively form a convex corner therebetween, said male corner defining a boundary between said distal-most portion of the proximal body and said proximal-most portion of the stem;
    a collar disposed on the proximal body and extending outward therefrom in a sideways direction with respect to the longitudinal axis of the stem to thereby define a ledge;
    wherein the ledge and the proximal body form an abrupt concave corner therebetween;
    wherein the male corner comprises an abrupt transition between the stem and the proximal body that is sufficiently abrupt in dimension and configuration to stimulate bone ingrowth, to a greater degree than bone ingrowth occurring about the stem, when implanted within the hollow interior portion of the first bone;
    wherein the distal-most portion of the proximal body is wider in a medial-lateral dimension than the stem in said medial-lateral dimension;
    wherein the convex corner comprises a circumferential male corner;
    wherein the circumferential convex corner defines a circle;
    wherein the distal-most portion of the proximal body is at least two millimeters wider than the proximal-most portion of the stem;
    wherein the collar, proximal body and stem cooperatively define a first collective length, and wherein the convex corner is spaced apart from a proximal-most portion of the collar by a distance of at least one-fourth of said first collective length;
    wherein the stem tapers inwardly from the convex corner in a proximal-to-distal direction to thereby define a concave area;
    wherein the tapering of the stem further comprises a circumferential, radial inward tapering to thereby define a circumferential concave area;

wherein the collar extends outward from the proximal body in a medial direction and in a posterior direction and in an anterior direction such that the ledge comprises a tri-directional, continuous medial-posterior-anterior overhang;

wherein the overhang has a flared, non-planer undersurface, and wherein the proximal body has a flared exterior surface defining a non-cylindrical, flared shape such that said proximal body and the flared, non-planer undersurface of the overhang cooperatively define a doubleflared contact surface to thereby enable subsidable engagement of said double-flared contact surface at two different rates of subsidence;

wherein the flared exterior surface of the proximal body defines at least a majority of a frustoconical shape;

wherein the collar is characterized by an absence of any lateral overhang and wherein the posterior and anterior portions of said overhang each terminate in the lateral direction at a terminal posterior point and a terminal anterior point, respectively, along posterior and anterior sides of the proximal body, respectively, to thereby define a spacial posterior gap and a spacial anterior gap between the lateral side of the proximal body and said terminal posterior point and terminal anterior point, respectively;

wherein a majority length of the stem defines a common, non-varying radius.

* * * * *